(12) United States Patent
Meller et al.

(10) Patent No.: US 8,764,683 B2
(45) Date of Patent: Jul. 1, 2014

(54) MEDICAL DEVICE GUIDEWIRE WITH A POSITION SENSOR

(75) Inventors: Nimrod Meller, Kiryat Tivon (IL); Ran Sela, Tel Aviv-Yafo (IL); Dan Seter, Haifa (IL); Lior Sobe, Kadima (IL)

(73) Assignee: Mediguide Ltd., Haifa (IL)

( * ) Notice: Subject to any disclaimer, the term of this patent is extended or adjusted under 35 U.S.C. 154(b) by 138 days.

(21) Appl. No.: 12/980,848

(22) Filed: Dec. 29, 2010

(65) Prior Publication Data

US 2012/0172761 A1 Jul. 5, 2012

(51) Int. Cl.
*A61M 25/09* (2006.01)

(52) U.S. Cl.
USPC ............ 600/585; 600/410; 600/411; 600/424

(58) Field of Classification Search
USPC .................. 600/410, 411, 585, 424
See application file for complete search history.

(56) References Cited

U.S. PATENT DOCUMENTS

| | | | |
|---|---|---|---|
| 4,941,473 A | 7/1990 | Tenerz et al. | |
| 5,184,621 A | 2/1993 | Vogel et al. | |
| 5,596,996 A | 1/1997 | Johanson et al. | |
| 5,701,905 A * | 12/1997 | Esch | 600/486 |
| 5,740,808 A * | 4/1998 | Panescu et al. | 600/424 |
| 5,924,997 A * | 7/1999 | Campbell | 600/549 |
| 6,233,476 B1 | 5/2001 | Strommer et al. | |
| 6,498,944 B1 | 12/2002 | Ben-Haim et al. | |
| 6,565,514 B2 | 5/2003 | Svanerudh et al. | |
| 6,788,967 B2 | 9/2004 | Ben-Haim et al. | |
| 6,908,442 B2 * | 6/2005 | von Malmborg et al. | 600/585 |
| 7,025,734 B1 | 4/2006 | Ellis et al. | |
| 7,197,354 B2 | 3/2007 | Sobe | |
| 7,386,339 B2 | 6/2008 | Strommer et al. | |
| 7,472,601 B1 | 1/2009 | Tenerz et al. | |
| 7,494,687 B2 * | 2/2009 | Cox | 427/2.24 |
| 7,645,233 B2 | 1/2010 | Tulkki et al. | |
| 7,724,148 B2 | 5/2010 | Samuelsson et al. | |
| 7,775,988 B2 | 8/2010 | Pijls | |
| 7,951,093 B2 * | 5/2011 | Skujins et al. | 600/585 |
| 7,967,761 B2 * | 6/2011 | Smith | 600/585 |
| 8,239,003 B2 * | 8/2012 | Akins | 600/424 |
| 8,343,076 B2 * | 1/2013 | Sela et al. | 600/585 |
| 8,579,825 B2 * | 11/2013 | Tenerz et al. | 600/488 |
| 2001/0051769 A1 * | 12/2001 | Hoek et al. | 600/381 |
| 2002/0013527 A1 | 1/2002 | Hoek et al. | |

(Continued)

FOREIGN PATENT DOCUMENTS

EP 2 085 108 1/2009
WO 93/12718 7/1993

OTHER PUBLICATIONS

"International Search Report & Written Opinion", PCT/US2011/056633 Feb. 1, 2012.

(Continued)

*Primary Examiner* — Sean Dougherty
(74) *Attorney, Agent, or Firm* — Dykema Gossett PLLC

(57) ABSTRACT

A guidewire for a medical device is disclosed. In one embodiment, the guidewire includes a corewire having a proximal end portion and a distal end portion, an elongate shroud disposed about the corewire, the shroud having a distal end, and a plug coupled with the distal end portion of the corewire and the distal end of the shroud, the plug having a distal, non-traumatic tip portion, an interior between the corewire and the shroud being configured to receive a sensor.

24 Claims, 7 Drawing Sheets

(56) References Cited

U.S. PATENT DOCUMENTS

| | | |
|---|---|---|
| 2004/0097804 A1 | 5/2004 | Sobe |
| 2004/0116816 A1* | 6/2004 | Tenerz et al. ............... 600/486 |
| 2005/0070793 A1* | 3/2005 | Pacetti et al. ............... 600/431 |
| 2005/0096567 A1* | 5/2005 | Reynolds et al. ............ 600/585 |
| 2005/0107688 A1 | 5/2005 | Strommer |
| 2005/0145307 A1* | 7/2005 | Shireman et al. ............ 148/565 |
| 2005/0197557 A1 | 9/2005 | Strommer et al. |
| 2006/0079740 A1* | 4/2006 | Silver et al. ................. 600/309 |
| 2006/0129041 A1* | 6/2006 | Ellis et al. ................... 600/341 |
| 2006/0189896 A1* | 8/2006 | Davis et al. .................. 600/585 |
| 2006/0241505 A1 | 10/2006 | Ahmed et al. |
| 2006/0282016 A1* | 12/2006 | Cornelius et al. ............ 600/585 |
| 2007/0208251 A1* | 9/2007 | Anderson et al. ............ 600/424 |
| 2007/0208252 A1 | 9/2007 | Makower |
| 2007/0299424 A1 | 12/2007 | Cumming et al. |
| 2008/0021347 A1* | 1/2008 | Jacobsen et al. ............. 600/585 |
| 2008/0021348 A1* | 1/2008 | Jacobsen et al. ............. 600/585 |
| 2008/0132806 A1 | 6/2008 | Smith |
| 2008/0255446 A1* | 10/2008 | Akins ........................... 600/424 |
| 2009/0112128 A1* | 4/2009 | Schiff et al. .................. 600/585 |
| 2009/0118643 A1* | 5/2009 | Smith et al. .................. 600/585 |
| 2009/0192412 A1 | 7/2009 | Sela et al. |
| 2009/0192413 A1 | 7/2009 | Sela et al. |
| 2009/0292225 A1* | 11/2009 | Chen et al. ................... 600/585 |
| 2010/0030114 A1* | 2/2010 | Nguyen et al. ............... 600/585 |

OTHER PUBLICATIONS

Supplementary European Search Report; EP 11854428; Publication date Mar. 19, 2014.

* cited by examiner

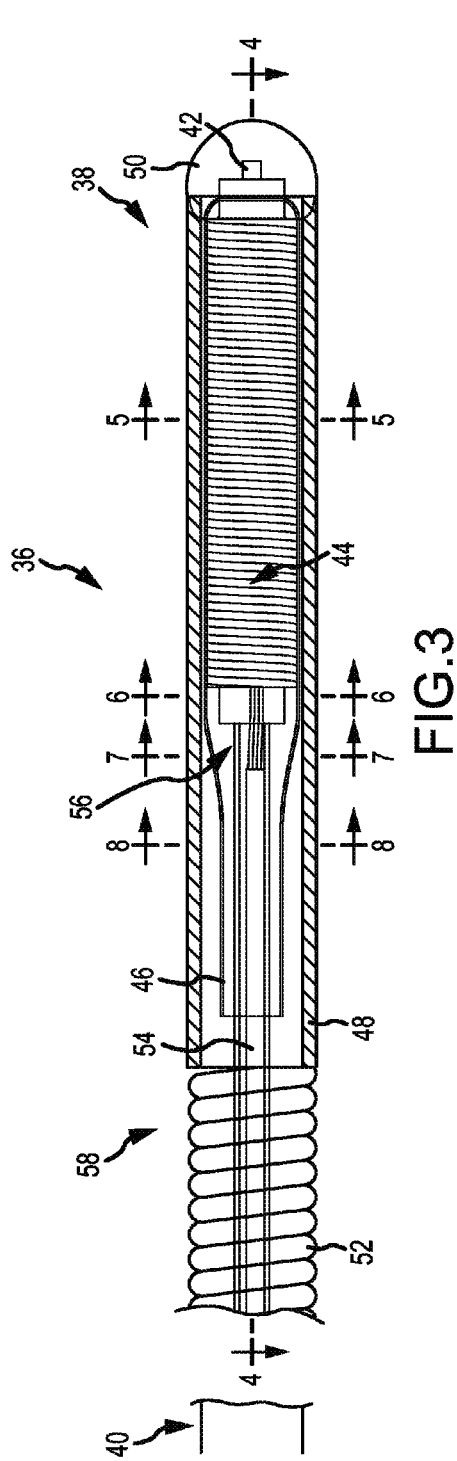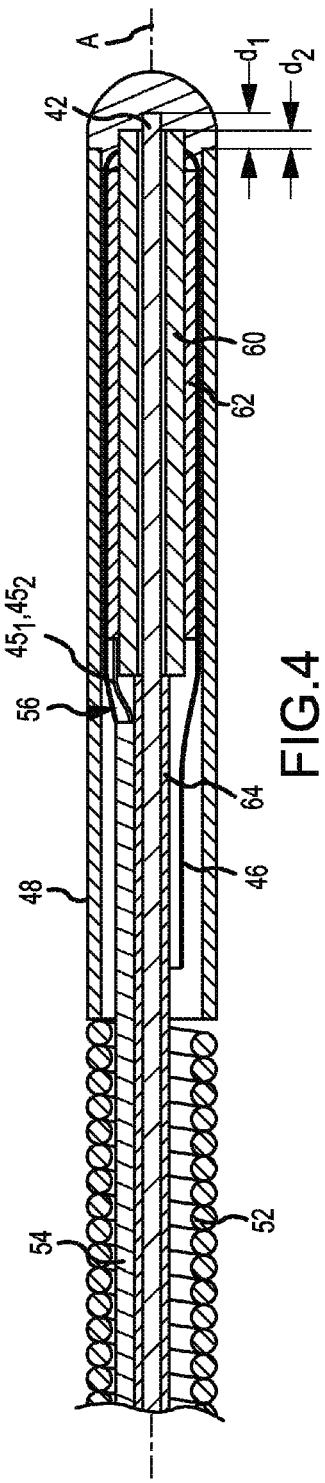

MEDICAL DEVICE GUIDEWIRE WITH A POSITION SENSOR

BACKGROUND OF THE INVENTION a. Field of the Invention

The instant invention relates generally to a medical device guidewire, and more specifically to a medical device guidewire with a position sensor.

b. Background Art

Various diagnostic and therapeutic procedures in or on the body of a patient, such as in the circulatory system, the gastrointestinal tract, the brain vessels, the bronchial tree or the like may be performed or facilitated by inserting a catheter into a body lumen and thereafter navigating the diagnostic or therapeutic catheter to the target anatomical site. To facilitate navigation of the catheter, a guidewire is often used. The guidewire typically has a reduced diameter relative to the catheter; the reduced diameter aids a physician in inserting and navigating the guidewire to the anatomical site. The catheter is then passed over the guidewire and guided to the target site.

One method for maneuvering a guidewire involves the use of fluoroscopy to track the position of a guidewire, particularly its distal tip, during navigation. Another method of maneuvering a guidewire to an operational site is to place one or more position sensors on the guidewire, track the sensors with a navigation system, and display a real-time or rendered image of the guidewire for the clinician manipulating the guidewire to view. One such system for maneuvering a guidewire is detailed in commonly assigned European Patent Application Publication EP 2 085 108 A2 entitled "SENSOR MOUNTED FLEXIBLE GUIDEWIRE", which is hereby incorporated by reference in its entirety.

Repeated contact between the tip of the guidewire and anatomical features of the patient during navigation is inevitable. Such contact can place unwanted stress on the structure of the guidewire and potentially damage the guidewire. To reduce instances of contact while maneuvering a guidewire to a target anatomical region, it is desirable for a clinician to be able to "see" the extreme distal tip of the guidewire. Accordingly, in embodiments where the guidewire is tracked by a navigation and positioning system, it is desirable to place a position sensor as close to the distal tip of the guidewire as possible. Moreover, regardless of the location of the position sensors on the guidewire, it is also desirable to protect the position sensor(s) and associated wiring from bending-induced stress as well as from exposure to body fluids to ensure reliable electrical function of the sensors.

There is therefore a need for an improved guidewire that minimizes or eliminates one or more problems as set forth above.

BRIEF SUMMARY OF THE INVENTION

One advantage of the methods and apparatus described, depicted, and claimed herein relates to a reduction in the stress experienced in or by the position sensor and related wiring in a medical device when the device is subjected to bending or deflection. Another advantage involves improved accuracy due to the improvements made in locating the position sensor nearer to the extreme distal end of the medical device in which the sensor is disposed.

This disclosure is directed to a guidewire for a medical device. In one embodiment, the guidewire includes a corewire having a proximal end portion and a distal end portion, an elongate shroud disposed about the corewire, the shroud having a distal end, and a plug coupled with the distal end portion of the corewire and the distal end of the shroud, the plug having a distal, non-traumatic tip portion, an interior between the corewire and the shroud being configured to receive a sensor. Most of the bending-induced stress is absorbed by the corewire, not the sensor or its connecting wire, thus reducing the incidence of sensor and/or connection failure. In addition, the shroud protects the sensor and its wiring connection from instances of direct contact, as well as from exposure to fluids, thus improving reliability.

In another embodiment, the guidewire includes a corewire having a distal end portion and a proximal end portion, the distal end portion having a distal tip, and an elongate shroud disposed about the distal end portion of the corewire, the shroud having a distal end and a proximal end. The guidewire further includes a plug coupled with the distal end portion of the corewire and coupled with the distal end of the shroud for creating a non-traumatic distal tip of the guidewire, and a tubular spring disposed about the distal end portion of the corewire proximal to the proximal end of the shroud, wherein the spring is configured to support compressive and tensile loads.

These and other benefits, features, and capabilities are provided according to the structures, systems, and methods depicted, described and claimed herein.

BRIEF DESCRIPTION OF THE DRAWINGS

FIG. 3 is a diagrammatic view of a first guidewire embodiment.

FIG. 4 is a cross-sectional view of the first guidewire embodiment, taken substantially along line 4-4 in FIG. 3.

DETAILED DESCRIPTION OF THE INVENTION

Figure 1:
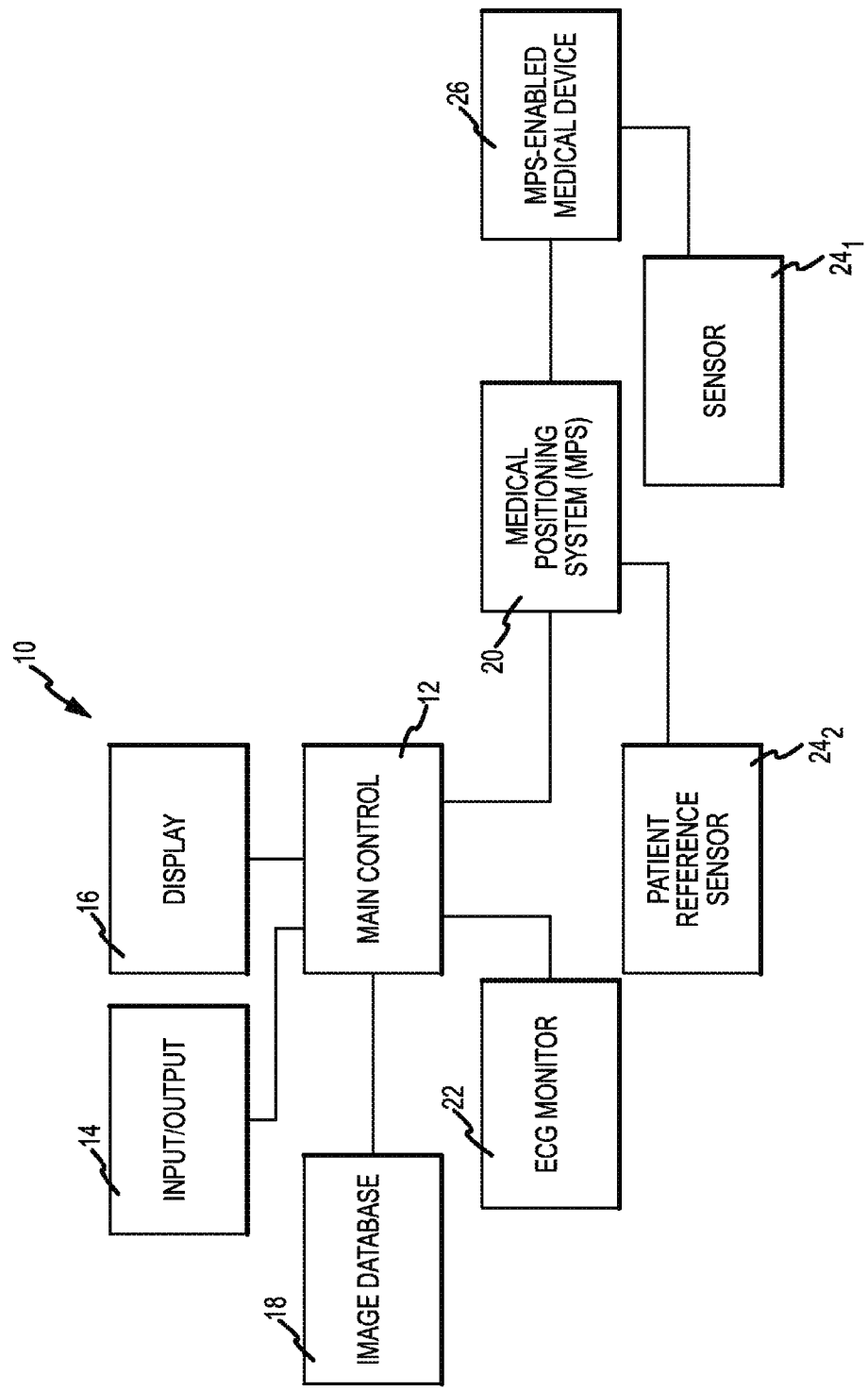
FIG. 1 is a schematic and block diagram view of a system incorporating an embodiment of a guidewire with a hollow coil position sensor.

Referring now to the drawings wherein like reference numerals are used to identify identical components in the various views, FIG. 1 is a diagrammatic view of a system 10 in which a position sensing guidewire may be used. System 10 as depicted includes a main electronic control unit 12 (e.g., a processor) having various input/output mechanisms 14, a display 16, an optional image database 18, a localization system such as a medical positioning system (MPS) 20, an electrocardiogram (ECG) monitor 22, one or more MPS location sensors respectively designated $24_1$ and $24_2$, and an MPS-enabled guidewire 26 which itself includes one and optionally more MPS location sensors, shown in exemplary fashion as having one such sensor $24_1$.

Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Embodiments consistent with the invention may find use in navigation applications that use imaging of a region of interest. Therefore system 10 may optionally include image database 18. Image database 18 may be configured to store image information relating to the patient's body, for example a region of interest surrounding a destination site for medical device 26 and/or multiple regions of interest along a navigation path contemplated to be traversed by device 26 to reach the destination site. The image data in database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from ECG monitor 22. It should be understood that the foregoing are examples only and not limiting in nature. For example, the image database may also include three-dimensional image data as well. It should be further understood that the images may be acquired through any imaging modality, now known or hereafter developed, for example X-ray, ultrasound, computerized tomography, nuclear magnetic resonance or the like.

MPS 20 is configured to serve as the localization system and therefore to determine positioning (localization) data with respect to one or more of MPS location sensors $24i$ (where i=1 to n) and output a respective location reading. The location readings may each include at least one or both of a position and an orientation (P&O) relative to a reference coordinate system, which may be the coordinate system of MPS 20. For example, the P&O may be expressed as a position (i.e., a coordinate in three axes X, Y and Z) and orientation (i.e., an azimuth and elevation) of a magnetic field sensor in a magnetic field relative to a magnetic field generator(s) or transmitter(s).

Figure 2:
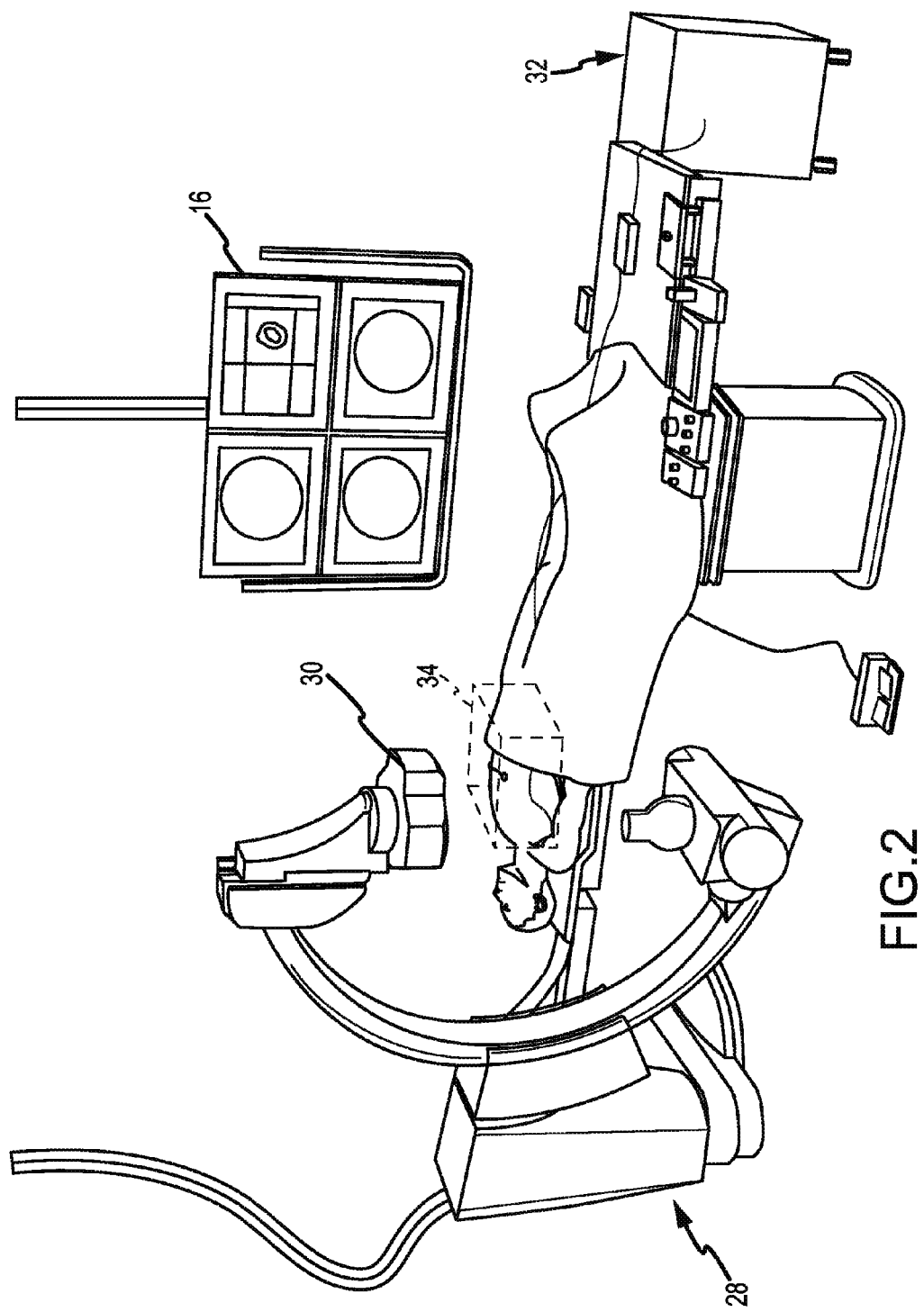
FIG. 2 is a diagrammatic view of an exemplary catheter-lab environment in which the system of FIG. 1, particularly including the MPS-enabled guidewire, may be used.

MPS 20 determines respective locations (i.e., P&O) in the reference coordinate system based on capturing and processing signals received from the magnetic field sensors $24i$ while such sensors are disposed in a controlled low-strength AC magnetic field (see FIG. 2). From an electromagnetic perspective, these sensors develop a voltage that is induced on the coil residing in a changing magnetic field, as contemplated here. Sensors $24i$ are thus configured to detect one or more characteristics of the magnetic field(s) in which they are disposed and generate an indicative signal, which is further processed by MPS 20 to obtain a respective P&O thereof. Exemplary design features and manufacturing processes and methods for sensors $24i$ and medical devices incorporating such sensors are known in the art.

MPS sensor $24_1$, and optionally additional MPS sensors in further embodiments, may be associated with MPS-enabled medical device 26. Another MPS sensor, namely, patient reference sensor (PRS) $24_2$ (if provided in system 10) is configured to provide a positional reference of the patient's body so as to allow motion compensation for gross patient body movements and/or respiration-induced movements. PRS $24_2$ may be attached to the patient's manubrium sternum, a stable place on the chest, or another location that is relatively positionally stable. Like MPS location sensor $24_1$, PRS $24_2$ is configured to detect one or more characteristics of the magnetic field in which it is disposed wherein MPS 20 provides a location reading (e.g., a P&O reading) indicative of the PRS's position and orientation in the reference coordinate system.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit 12 for ECG synchronized play-back of a previously captured sequence of images (cine loop) stored in database 18. ECG monitor 22 and ECG-electrodes may both comprise conventional components.

FIG. 2 is a diagrammatic view of system 10 as incorporated into a larger system, namely, a catheter lab. It should be understood that while embodiments may be used in the catheter-lab environment to be described below, this is exemplary only and not limiting in nature. MPS 20 includes a magnetic transmitter assembly (MTA) 30 and a magnetic processing core 32 for determining location (P&O) readings. MTA 30 is configured to generate the magnetic field(s) in and around the patient's chest cavity, in a predefined three-dimensional space identified as a motion box 34. MPS sensors 24, as described above are configured to sense one or more characteristics of the magnetic field(s) and when the sensors are in motion box 34, each generate a respective signal that is provided to magnetic processing core 32. Processing core 32 is responsive to these detected signals and is configured to calculate respective P&O readings for each MPS sensor $24i$ in motion box 34. Thus, MPS 20 enables real-time tracking of each sensor $24i$ in three-dimensional space.

The positional relationship between the image coordinate system and the MPS reference coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly coordinated with any particular image being used. One exemplary embodiment of an MPS 20 will be described in greater detail below in connection with FIG. 11.

FIG. 3 is a diagrammatic view of a first embodiment of a guidewire 36 that may be used as device 26 in system 10, with portions of a shroud broken away to more clearly show the interior components. Guidewire 36 has a distal end 38 and a proximal end 40. As used with reference to a guidewire, "distal" refers to an end that is advanced to the region of interest within a body while "proximal" refers to the opposite end that is disposed outside of the body and manipulated manually by a clinician or automatically through, for example, robotic controls.

Guidewire 36 includes a central corewire 42 and a generally thin-walled elongate shroud 48 defining an interior which contains corewire 42 and is configured in size and shape to receive a sensor 44. Sensor 44, and optionally a sheath 46 surrounding sensor 44, are disposed within the interior. In the illustrated embodiment, corewire 42 extends through sensor 44. A plug 50 is provided at the extreme distal end of guidewire 36 for structural support and to provide for non-traumatic contact of the tip when introducing and navigating the guidewire through a lumen of a patient. Plug 50 is preferably rounded and may be made of polymer, glue, bonding material, metal, or any other relatively smooth material suitable for this purpose. Plug 50 is shown in a hemispherical shape, but may be in any other non-traumatic form. Plug 50 may be coupled to one or more of corewire 42, sensor 44, and shroud 48 by gluing, bonding, welding, soldering, or another patient-safe coupling method. Alternatively, plug 50 may be a formed part of shroud 48. Wiring 54 is coupled to sensor 44 at a connection node 56. Wiring 54 extends towards guidewire proximal end 40 to provide electrical connectivity between guidewire proximal end 40 and sensor 44. Wiring 54 may be coupled to sensor 44 by soldering or another electrically-connective coupling method.

Shroud 48 is provided at guidewire distal end 38 to protect the interior of the distal assembly from compressive and tensile loads resulting from insertion, removal, and bending of guidewire 36. Accordingly, both sensor 44 and connection node 56 are axially distal (i.e., forward) of the proximal end (i.e., rear) of shroud 48. Shroud 48 may be made of a rigid material, such as platinum or another biocompatible metal or alloy, which advantageously provides rigidity around sensor 44 and connection node 56. Shroud 48 may also be radiopaque (e.g., platinum and/or its alloys), increasing the fluoroscopic visibility of distal end 38.

The illustrated embodiment of shroud 48 is exemplary only, and should not be construed as limiting. Although shroud 48 is shown as a thin-walled tube of constant diameter, shroud 48 may have another shape or cross-section, which may be constant or may vary along its axial length, and still fall within the scope of the present invention. Additionally, shroud 48 may comprise materials other than metal, may or may not be radiopaque, and may provide varying degrees of rigidity.

To provide bending flexibility, a spring 52 is located proximally of shroud 48. Spring 52 may be a radiopaque metal, such as platinum, to increase fluoroscopic visibility. Spring 52 may also be made of stainless steel, iridium, or nickel titanium alloys (i.e., Nitinol). In addition to providing flexibility and fluoroscopic visibility, spring 52 also protects wiring 54 that is proximally located with respect to shroud 48. The distal end of spring 52 may be coupled to the proximal end of shroud 48 by welding, soldering, with an adhesive such as medical grade epoxy, or with another patient-safe (biocompatible) coupling method. As shown, spring 52 is of substantially the same outside diameter as shroud 48 and thus maintains and extends in a proximal direction an outer diameter envelope established by shroud 48. However, spring 52 may have a different shape and/or different outside diameter and still fall within the scope of the present invention. Additionally, the illustrated embodiment is not intended to limit the structure of spring 52 as to coil width, spacing between coils (if any), or amount of flexibility. In an alternate embodiment, spring 52 may be a flexible polymer tube or a braided plastic tube.

FIG. 4 is a cross-section of guidewire 36 taken substantially along line 4-4 in FIG. 3. Corewire 42, in the illustrated embodiment, is located at the radial center of guidewire 36. In other words, the central longitudinal axis of corewire 42 is substantially the same as or coincident with the central axis "A" of guidewire 36. Corewire 42 has a distal end portion 58 (best shown in FIG. 3) which, in the illustrated embodiment, substantially coincides with guidewire distal end 38, and is at least as co-extensive as the axial extent of shroud 48 and spring 52. Corewire 42 further includes a proximal end portion. An extreme distal end of corewire 42 may be flush with or may extend distally a distance $d_1$ past the distal end of shroud 48. Corewire 42 may comprise a flexible wire of changing radial cross-sectional diameter, decreasing in diameter from its proximal end to its distal end, though the decrease is not illustrated. In distal end portion 58, corewire 42 has a circular cross-section of constant diameter (best seen in FIGS. 5-8). Corewire 42 advantageously distributes bending stresses, tensile loads, and compressive loads over its length, reducing stress on the other components of guidewire 36 such as wiring 54. In other words, loads (e.g., due to contact with tissue) imposed on shroud 48 are transferred via tip 50 to corewire 42, and similarly loads directly imposed on tip 50 are likewise resolved through corewire 42. Corewire 42 may be made of metal, such as stainless steel, titanium, or nickel titanium alloys (i.e., Nitinol), or other biocompatible material. To fully distribute bending stresses over the entire length of guidewire 36, corewire 42 may be a single continuous wire extending the entire axial length of guidewire 36. However, corewire 42 may also be a multi-piece construction, such as the construction described in commonly-assigned United States Patent Application Publication 2009/0192413, hereby incorporated by reference in its entirety.

The illustrated embodiment of corewire 42 is intended to be exemplary only and not limiting. Many variations could be made to corewire 42 and still fall within the scope and spirit of the claimed invention. For example, corewire 42 may comprise a material other than metal and may have a non-circular cross-section. Additionally, corewire 42 may be solid, hollow, or have some other interior construction.

With continued reference to FIG. 4, sensor 44 is located radially-outwardly from corewire 42 and may comprise multiple elements, or may be unitary. In the illustrated first embodiment, sensor 44 comprises a hollow cylindrical sensor core 60 and a wire wound on sensor core 60 to form a coil 62 with two free ends thereof forming leads $45_1$, $45_2$ which are available at the sensor's proximal end. The two leads are electrically connected to wiring 54 at connection node 56. Wiring 54 and connection node 56 are electrically insulated from corewire 42 by an electrical insulating layer 64, which may be a polymer tube slipped or shrunk on the corewire, a sprayed or applied layer of polymer or adhesive, or some other electrically insulating structure. Sensor core 60 may be a tube comprising magnetically permeable material, with the tube having a central lumen through which corewire 42 passes. The core 60 comprising magnetically-permeable material increases the overall sensitivity of the coil/core combination that forms positioning sensor 44 (as compared to the same coil configuration without a magnetically-permeable core). Sensor core 60 may be made of a metal alloy of magnetically-permeable material, such as an alloy of nickel and iron. The proximal end of sensor 44 is protected by shroud 48—in other words, sensor 44 is axially distal of the proximal end of shroud 48. In contrast, however, the distal end of sensor 44 may not be completely within the envelope defined by the shroud, as core 60 may extend slightly distally beyond the distal end of shroud 48 by a distance $d_2$. However, the distal end of sensor 44 is coupled to and is protected by plug 50. Optionally, tubular sheath 46 may be provided around (and surrounding) both the sensor 44 and connection node 56 for further protection and electrical insulation. Sheath 46 may be a polymer shrink tube or another electrically insulating structure or material.

Although sensor 44 is depicted and described as being a coil/core assembly, it should be understood that other types of position sensors may be used and remain within the spirit and scope of the present invention. In the case of a coil sensor, variations as to the number of coils, their geometries, spatial relationships, the existence or absence of cores and the like are possible. Although only one sensor 44 is shown on guidewire 36, multiple sensors 44 could be placed on guidewire 36, at distal end 38 or other locations on guidewire 36. Additionally, multiple sensor positions and orientations relative to other elements of guidewire 36 are possible. For instance, sensor 44 may extend distally beyond the distal end of shroud 48, or shroud 48 may extend distally beyond the distal end of sensor 44. Likewise, either shroud 48 or sensor 44 may extend proximally beyond the other. Furthermore, in an embodiment where guidewire 36 is device 26 for use in system 10, sensor 44 may be MPS sensor $24_1$. A function of sensor 44, in the context of a magnetic field based positioning system, is to detect one or more characteristics of the magnetic field(s) in which it is placed. In this regard, one of ordinary skill in the art will appreciate there are many variations and configurations.

Figure 5:
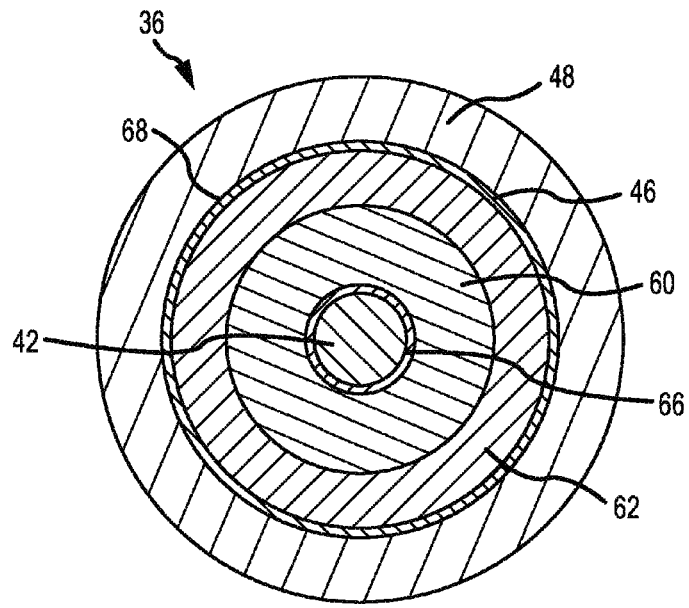
FIG. 5 is a cross-sectional view of the first guidewire embodiment, taken substantially along line 5-5 in FIG. 3.
Figure 6:
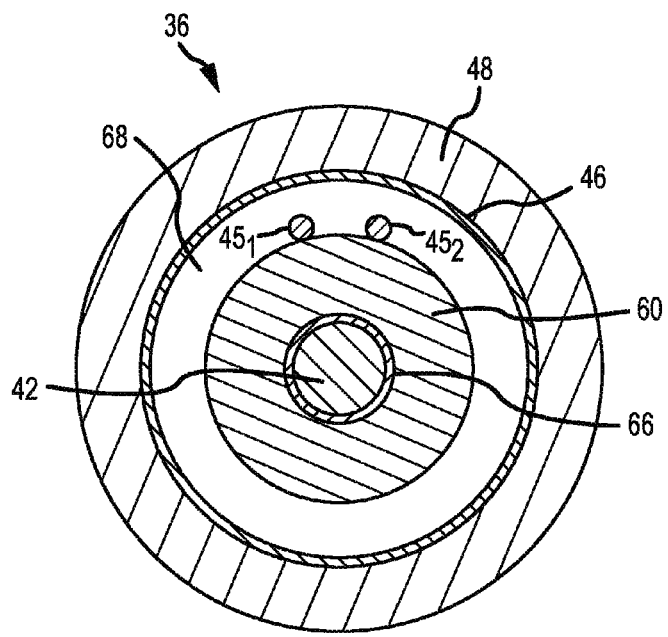
FIG. 6 is a cross-sectional view of the first guidewire embodiment, taken substantially along line 6-6 in FIG. 3.
Figure 7:
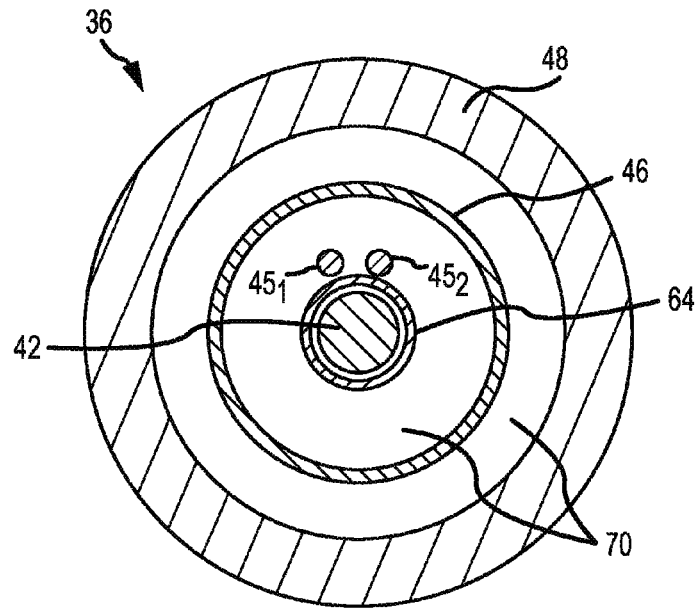
FIG. 7 is a cross-sectional view of the first guidewire embodiment, taken substantially along line 7-7 in FIG. 3.
Figure 8:
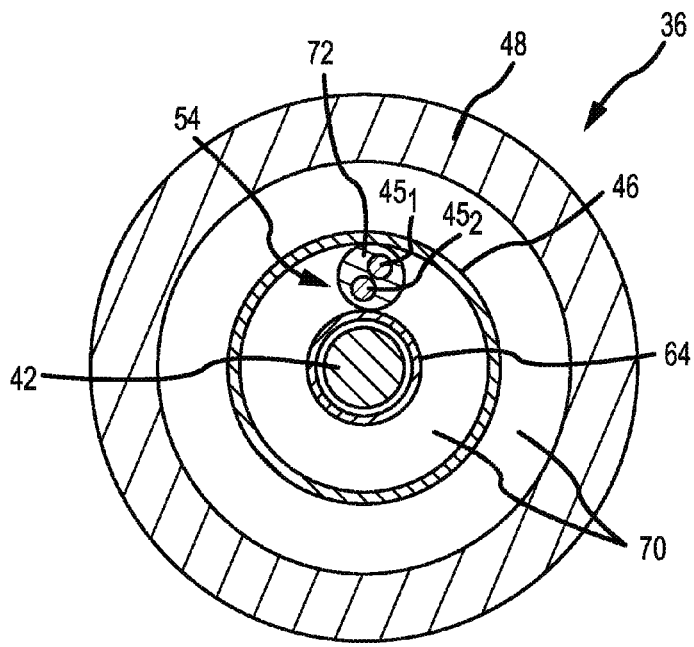
FIG. 8 is a cross-sectional view of the first guidewire embodiment, taken substantially along line 8-8 in FIG. 3.

FIGS. 5-8 illustrate various radial cross-sections of guidewire 36. FIG. 5 shows a portion of distal end 38 in which sensor 44 is disposed, taken substantially along line 5-5 in FIG. 3. FIGS. 6 and 7 illustrate cross-sections of connection node 56. FIG. 8 illustrates an exemplary structure of wiring 54 axially proximal of connection node 56.

Referring to FIG. 5, in the illustrated embodiment, each one of corewire 42, sensor core 60, coil 62, sheath 46, and shroud 48 has a circular cross-section. Shroud 48 is radially symmetrical about corewire 42, which advantageously reduces whiplash effects as guidewire 36 experiences variable amounts and orientations of torque and bending. A first clearance 66 separates corewire 42 from sensor core 60. First clearance 66 may be filled with an encapsulant, such as adhesive-type, electrically-insulative medical grade epoxy, to couple sensor core 60 with corewire 42, yet electrically insulate the two. A second clearance 68 may separate sensor 44 from shroud 48. If used, sheath 46 may be disposed in second clearance 68. Second clearance 68 (including any clearance inside and/or outside of sheath 46) may also be filled with the above-mentioned encapsulant to solidify the assembly. In an embodiment, the entire distal end portion of guidewire 36 may be "potted" simultaneously, wherein the above-mentioned encapsulant is introduced (e.g., from the extreme distal end) into the interior of shroud 48. The foregoing is effective in filling the above-mentioned clearances, fixing the various components together while also providing protection from environmental influences that may be encountered during usage.

FIG. 6 is a cross-sectional view of guidewire 36 taken substantially along line 6-6 in FIG. 3. FIG. 6 illustrates the free ends or leads $45_1$, $45_2$ of coil 62 that are destined for electrical connection to corresponding leads of wiring 54. As shown, coil leads $45_1$, $45_2$ pass over sensor core 60 at connection node 56. Corewire 42, sensor core 60, sheath 46, and shroud 48 have substantially the same diameter and cross-section as in the more distal cross-section shown in FIG. 5. As a result, advantageous radial symmetry is maintained. As in FIG. 5, first clearance 66 and second clearance 68 may be filled with an encapsulant to couple corewire 42, sensor core 60, and sheath 46 within shroud 48.

FIG. 7 is a cross-sectional view of guidewire 36 taken substantially along line 7-7 in FIG. 3. FIG. 7 further illustrates coil leads $45_1$, $45_2$ that connect to wiring 54 as the leads pass over corewire 42 at connection node 56. Note that coil leads $45_1$, $45_2$ are somewhat closer together in FIG. 7, as leads $45_1$, $45_2$ approach wiring housing 72 (best shown in FIG. 8). Like FIGS. 5 and 6, advantageous radial symmetry is maintained. Sensor core 60 (and any insulating material between sensor core 60 and corewire 42) no longer separates connection node 56 from corewire 42, so insulating layer 64 is provided to electrically insulate corewire 42 from connection node 56. A small gap is shown between corewire 42 and insulating layer 64, but such a gap may not be present in finished guidewire 36. Insulating layer 64 may be tightly affixed to corewire 42, or insulating layer 64 may be applied loosely around corewire 42 and become tightly affixed as part of the process of constructing guidewire 36. For instance, insulating layer 64 may be a polymer shrink tube (shown in FIG. 7 as loose before a heating step in the manufacturing process) that later is heated and becomes tightly wrapped on corewire 42. A third clearance 70 separates corewire 42 (and insulating layer 64) from shroud 48. Like first clearance 66 and second clearance 68, third clearance 70 may be filled with an encapsulant, such as epoxy or other potting material, to couple one or more of corewire 42, insulating layer 64, connection node 56, sheath 46, and shroud 48.

FIG. 8 is a cross-sectional view of guidewire 36 taken substantially along line 8-8 in FIG. 3. FIG. 8 illustrates wiring 54 axially proximal of connection node 56. Wiring 54 may be 2-conductor twisted-pair (TP) including wires capable of transferring electrical signals from sensor 44 to proximal end 40. The wires of wiring 54 may have a thickness on the order of tens of micrometers, for example, between 10-25 µm. Wiring 54 may alternately comprise a coaxial cable, a flat flex cable, or other functionally comparable wiring including at least one wire. Wiring 54 is enclosed in a housing 72 disposed in third clearance 70. As in FIGS. 5-7, advantageous radial symmetry is maintained. An encapsulant may be disposed in third clearance 70 to bind the assembly.

Guidewire 36 may be constructed in a two step process. Corewire 42, sensor 44, wiring 54, and connection node 56 may first be potted inside sheath 46. The assembly encased in sheath 46 may then be potted inside shroud 48 and coupled to plug 50. If sheath 46 is omitted from guidewire 36, then corewire 42, sensor 44, wiring 54, and connection node 56 may be potted inside of shroud 48 in a single step and coupled to plug 50.

The illustrated embodiment of guidewire 36 provides many advantages. Corewire 42 absorbs and distributes tensile and compressive loads caused by insertion, removal, and bending of guidewire 36. For example, loads applied to the outer sheath are transferred via the plug 50 to corewire 36 and likewise loads applied directly to the plug 50 are also transferred to corewire 36. Some component of loads applied to the shroud are also resolved through spring 52; however, the point of emphasis is that the loads do not result in significant stress on either sensor 44 or the sensor coil/wiring connection node 56—components most sensitive to applied stresses. In sum, wiring 54 is not exposed to significant tensile and compressive loads or bending stress at any single point in the distal end of guidewire 36, ensuring reliable functionality of sensor 44. Shroud 48 protects sensor 44 and connection node 56 against bending stress and prevents fluids and other foreign objects from entering the interior of guidewire distal end 38. Plug 50 also protects against foreign object intrusion and bending stress in sensor 44 and connection node 56. Thanks to the protection and structural support provided by shroud 48, plug 50, and corewire 42, sensor 44 can be placed very close to the distal tip of guidewire 36, providing spatial positioning and orientation at the most useful location. Multiple sensors 44 may also be provided along the length of guidewire 36, increasing spatial positioning and orientation information without sacrificing other advantages. Additionally, the radial symmetry of distal end 38 reduces the likelihood of torque-induced whiplash.

Figure 9:
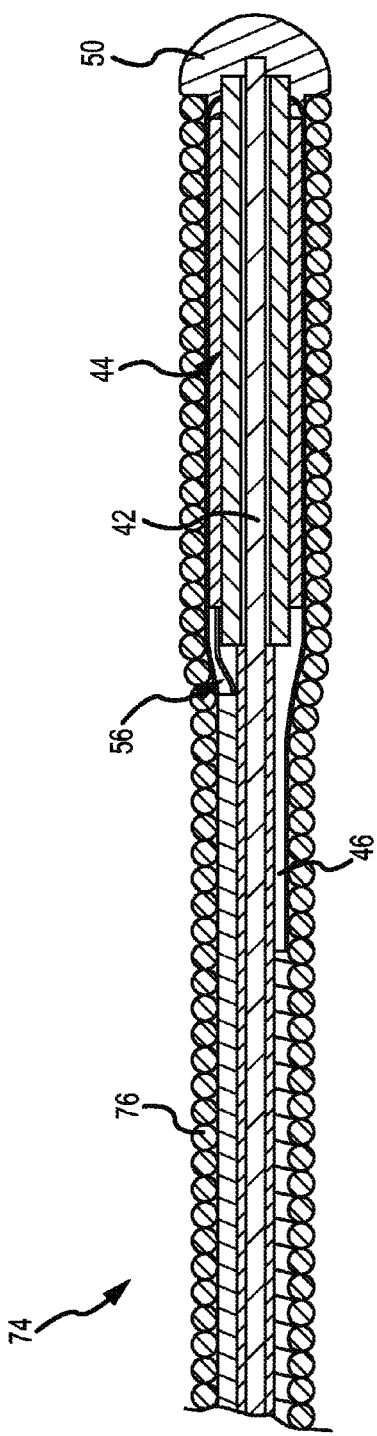
FIG. 9 is a cross-sectional view of a second guidewire embodiment.

FIG. 9 is a cross-sectional view of a second guidewire embodiment 74. The distal end of guidewire 74 is substantially the same as distal end 38 of guidewire 36, except guidewire 74 lacks a shroud. Instead, a tubular spring 76 extends to and may be coupled to plug 50. Corewire 42, sensor 44, sheath 46 (if provided), and connection node 56 all may be potted together inside spring 76. Spring 76 may comprise radiopaque material, such as platinum, to increase fluoroscopic visibility.

Figure 10:
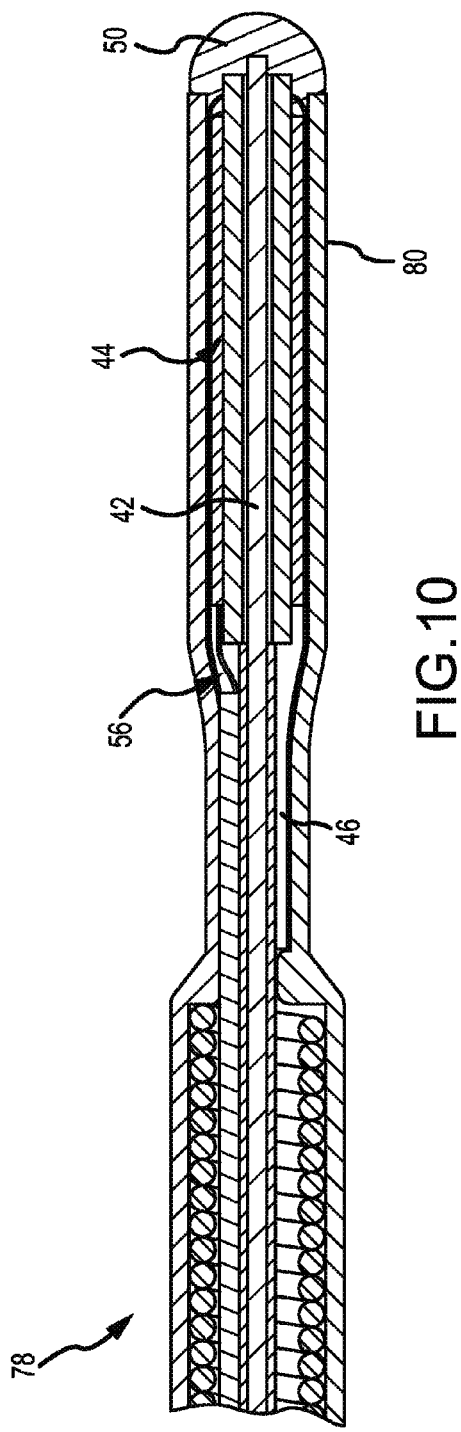
FIG. 10 is a cross-sectional view of a third guidewire embodiment.

FIG. 10 is a cross-sectional view of a third guidewire embodiment 78. The interior of the distal end of guidewire 78 is substantially the same as distal end 38 of guidewire 36. However, guidewire 78 lacks a shroud and in lieu thereof its distal end is covered by a coating 80. Coating 80 may comprise a polymer layer extending proximally from plug 50, covering sensor 44, wiring 54, and spring 52. Coating 80 completely circumferentially surrounds sensor 44 and connection node 56, just like shroud 48 (FIG. 3) and spring 76 (FIG. 9). Coating 80 advantageously seals the distal end of guidewire 80, rendering it watertight, and may be hydrophilic or hydrophobic. Coating 80 also creates a smooth, continuous surface which is advantageous in some applications, such as delivering pace-makers and other implantable device leads.

Figure 11:
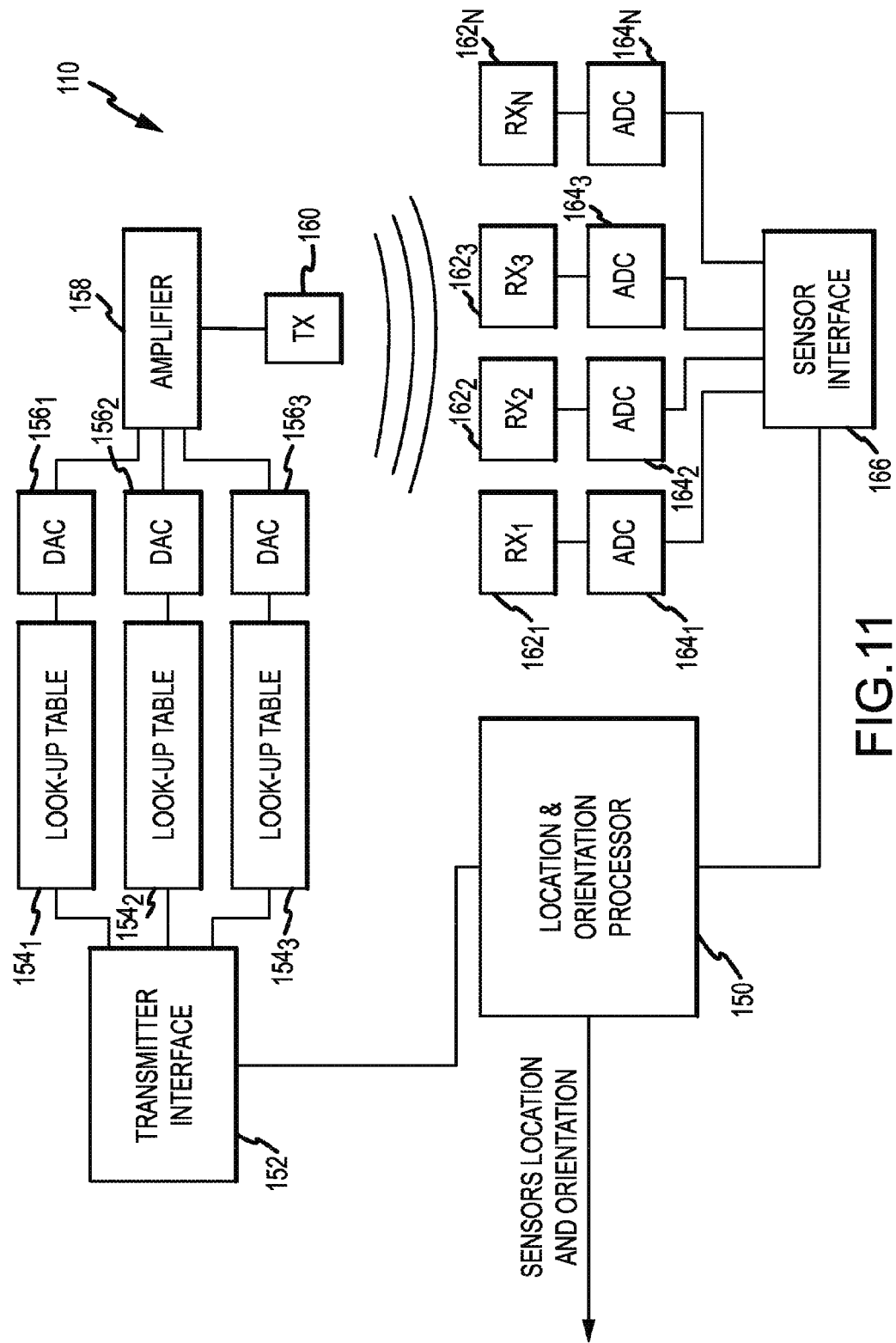
FIG. 11 is a schematic and block diagram view of one exemplary embodiment of a medical positioning system (MPS) as shown in block form in FIG. 1.

FIG. 11 is a schematic and block diagram of one exemplary embodiment of MPS 20, designated as an MPS 108, as also seen by reference to U.S. Pat. No. 7,386,339, referred to above, and portions of which are reproduced below, which generally describes, at least in part, the gMPS™ medical positioning system commercially offered by MediGuide Ltd. of Haifa, Israel and now owned by St. Jude Medical, Inc. It should be understood that variations are possible, for example, as also seen by reference to U.S. Pat. No. 6,233,476 entitled MEDICAL POSITIONING SYSTEM, also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, the following description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that system 10, particularly the main electronic control unit 12, as described above may include conventional processing apparatus known in the art, capable of executing pre-programmed instructions stored in an associated memory, all performing in accordance with the functionality described herein. Such an electronic control unit may further be of the type having both ROM, RAM, a combination of non-volatile and volatile (modifiable) memory so that any software may be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A guidewire comprising:
   a corewire having a proximal end portion and a distal end portion;
   an elongate shroud disposed about said corewire, said shroud having a distal end and a proximal end and defining a longitudinal axis extending through a center of said shroud from said shroud proximal end to said shroud distal end;

a plug coupled with said distal end portion of said corewire and said distal end of said shroud, said plug having a distal, non-traumatic tip portion; and a sensor disposed radially-outward of said corewire and radially-inward of said shroud, wherein said sensor comprises:
  a core comprising magnetically permeable material, said core having a lumen axially extending therethrough, said corewire extending through said lumen; and
  a coil disposed about said core;
  wherein said coil and said core form at least a portion of said sensor and are disposed radially-inward of said shroud.

2. The guidewire of claim 1, wherein said sensor is axially distal of said shroud proximal end.

3. The guidewire of claim 1, wherein a distal end of said sensor and a distal tip of said corewire are coupled to said plug.

4. The guidewire of claim 1, wherein a distal end of said sensor extends axially, distally beyond a distal end of said shroud.

5. The guidewire of claim 1, further comprising:
  at least one electrical wire connected to said sensor at a connection node;
  wherein said connection node is axially distal of said shroud proximal end.

6. The guidewire of claim 1, further comprising a sheath between said sensor and said shroud.

7. The guidewire of claim 1, wherein said shroud comprises radio-opaque material.

8. The guidewire of claim 1, further comprising an encapsulant disposed in (i) a first clearance between said corewire and said sensor and (ii) a second clearance between said sensor and said shroud.

9. The guidewire of claim 1, further comprising a tubular spring disposed about said corewire adjacent to a proximal end of said shroud.

10. The guidewire of claim 1, wherein said plug comprises a material selected from the group consisting of:
  metal;
  polymer;
  glue; and
  bonding material.

11. The guidewire of claim 1, wherein said proximal end portion of said corewire extends proximally of said shroud proximal end.

12. A guidewire comprising:
  a corewire having a distal end portion and a proximal end portion, said distal end portion having a distal tip;
  an elongate shroud disposed about said distal end portion of said corewire, said shroud having a distal end and a proximal end;
  a sensor disposed radially-outward of said corewire and radially-inward of said shroud;
  a plug coupled with said distal end portion of said corewire and coupled with said distal end of said shroud for creating a non-traumatic distal tip of said guidewire;
  a tubular spring having a distal end, said spring disposed about said distal end portion of said corewire, said spring distal end proximal of said proximal end of said shroud, wherein said spring is configured to support compressive and tensile loads; and
  wherein said spring distal end is coupled to said proximal end of said shroud.

13. The guidewire of claim 12, wherein said spring distal end is coupled to said proximal end of said shroud by at least one of:
  gluing;
  bonding;
  welding; and
  soldering.

14. The guidewire of claim 12, wherein an outer diameter of said spring is substantially equal to an outer diameter of said shroud.

15. The guidewire of claim 12, further comprising a sensor, wherein said sensor comprises:
  a core comprising magnetically permeable material, said core having a lumen extending therethrough, said corewire extending through said lumen; and
  a coil disposed about said core;
  wherein said core and said coil form at least a portion of said sensor and are radially-inward of said shroud.

16. A guidewire comprising:
  a corewire having a proximal end portion and a distal end portion;
  an elongate shroud disposed about said corewire, said shroud having a distal end and a proximal end and defining a longitudinal axis extending through the center of said shroud from said shroud proximal end to said shroud distal end;
  a plug coupled with said distal end portion of said corewire and said distal end of said shroud, said plug having a distal, non-traumatic tip portion;
  a sensor disposed radially-outward of said corewire and radially-inward of said shroud; and
  at least one electrical wire connected to said sensor at a connection node, wherein said connection node is axially distal of said shroud proximal end,
  wherein said proximal end portion of said corewire extends proximally of said shroud proximal end.

17. The guidewire of claim 16, wherein said at least one electrical wire comprises a twisted pair cable.

18. The guidewire of claim 16, wherein said sensor comprises:
  a core; and
  a coil disposed on said core.

19. The guidewire of claim 18, wherein said core comprises magnetically permeable material, said core having a lumen axially extending therethrough, said corewire extending through said lumen.

20. A guidewire comprising:
  a corewire having a proximal end portion and a distal end portion;
  an elongate shroud disposed about said corewire, said shroud having a distal end and a proximal end and defining a longitudinal axis extending through the center of said shroud from said shroud proximal end to said shroud distal end;
  a plug coupled with said distal end portion of said corewire and said distal end of said shroud, said plug having a distal, non-traumatic tip portion;
  a sensor disposed radially-outward of said corewire and radially-inward of said shroud; and
  a sheath between said sensor and said shroud,
  wherein said proximal end portion of said corewire extends proximally of said shroud proximal end.

21. The guidewire of claim 20, wherein said sensor comprises:
  a core; and
  a coil disposed on said core.

22. The guidewire of claim 21, wherein said core comprises magnetically permeable material, said core having a lumen axially extending therethrough, said corewire extending through said lumen.

23. A guidewire comprising:
- a corewire having a proximal end portion and a distal end portion;
- an elongate shroud disposed about said corewire, said shroud having a distal end and a proximal end and defining a longitudinal axis extending through the center of said shroud from said shroud proximal end to said shroud distal end;
- a plug coupled with said distal end portion of said corewire and said distal end of said shroud, said plug having a distal, non-traumatic tip portion;
- a sensor disposed radially-outward of said corewire and radially-inward of said shroud; and
- an encapsulant disposed in (i) a first clearance between said corewire and said sensor and (ii) a second clearance between said sensor and said shroud.

24. The guidewire of claim 23, further comprising a sheath between said sensor and said shroud.

\* \* \* \* \*